United States Patent [19]

Ottenheijm et al.

[11] Patent Number: 4,581,360
[45] Date of Patent: Apr. 8, 1986

[54] SPARSOMYCIN ($S_c$-$R_s$) DERIVATIVE; PHARMACEUTICAL COMPOSITION HAVING ANTI-TUMOR ACTIVITY

[75] Inventors: Henricus C. J. Ottenheijm, Milsbeek, Netherlands; Robertus M. J. Liskamp, New York, N.Y.

[73] Assignee: Stichting Katholieke Universiteit, Netherlands

[21] Appl. No.: 546,845

[22] Filed: Dec. 9, 1983

[30] Foreign Application Priority Data

Nov. 1, 1982 [NL] Netherlands ..................... 8204224

[51] Int. Cl.[4] .................. A61K 31/505; C07D 239/54; C12P 17/12; C12R 1/465
[52] U.S. Cl. .................................... 514/274; 435/122; 435/886; 435/905; 544/311
[58] Field of Search ................. 544/309, 311; 424/251; 514/274

[56] References Cited

PUBLICATIONS

Ottenheijm et al. *Tetrahedron Lett.* No. 4 pp. 387–390 (1979).
Ottenheijm et al. *Tetrahedron Lett.* No. 27 pp. 2437–2438, (1978).
Ottenheijm et al. *J. Org. Chem.* (1981), 46, pp. 3273–3283.
Liskamp et al. *J. Org. Chem.* (1981), 46, pp. 5408–5413.
Kuwano et al. *Biochem. Biophys. Acta* (1979) vol. 563 p. 479.
Baglioni *Biochem. Biophys. Acta* (1966) vol. 129 pp. 642–645.
Close et al. *Cancer Chemother. Rep.* No. 43 (1964) pp. 29–31.
Helquist et al. *J. Am. Chem. Soc.* (1979) vol. 101 pp. 1057–1059.
Goldberg et al. *Biochem. Biophys. Res. Comm.* vol. 23, No. 4 (1966) pp. 453–459.
Vince et al. *Biochem. Biophys. Res. Comm.* vol. 75, No. 3 (1977) pp. 563–567.
Argoudelis et al. *Antimicrob. Agents Chemother.* (1962) pp. 780–786.
Owen et al. *Antimicrob. Ag. Chemother.* (1962) pp. 772–779.
Liskamp et al. *Chemical Abstracts* 100: 79469z (1984).
Liskamp *Chemical Abstracts* 101: 130522m (1984).
Duke et al. *Chemical Abstracts* 99: 158096q (1983).
Upjohn Co. *Chemical Abstracts* 62: 5855d (1965).
Ash et al. *Chemical Abstracts* 101: 20417y (1984).
Duke *Diss Abs. Int* vol. 43, No. 10 Apr. 1983, p. 3949B.
Dah-Ren *Diss Abs. Int* vol. 43, No. 11, May 1983, p. 3597B.
Lin et al. *J. Med. Chem,* 1977, vol. 20, No. 3 pp. 337–341.

*Primary Examiner*—Donald G. Daus
*Assistant Examiner*—Stephen M. Kapner
*Attorney, Agent, or Firm*—Scully, Scott, Murphy & Presser

[57] ABSTRACT

The invention concerns novel sparsomycin ($S_c$-$R_s$) derivatives having superior cytostatic activity compared to sparsomycin itself. Said derivatives contain a lipophilic group $R^2$, selected from $C_2$-$C_{20}$-alkyl, aryl, aralkyl and alkaryl, which is preferably n-octyl or benzyl.

3 Claims, 7 Drawing Figures

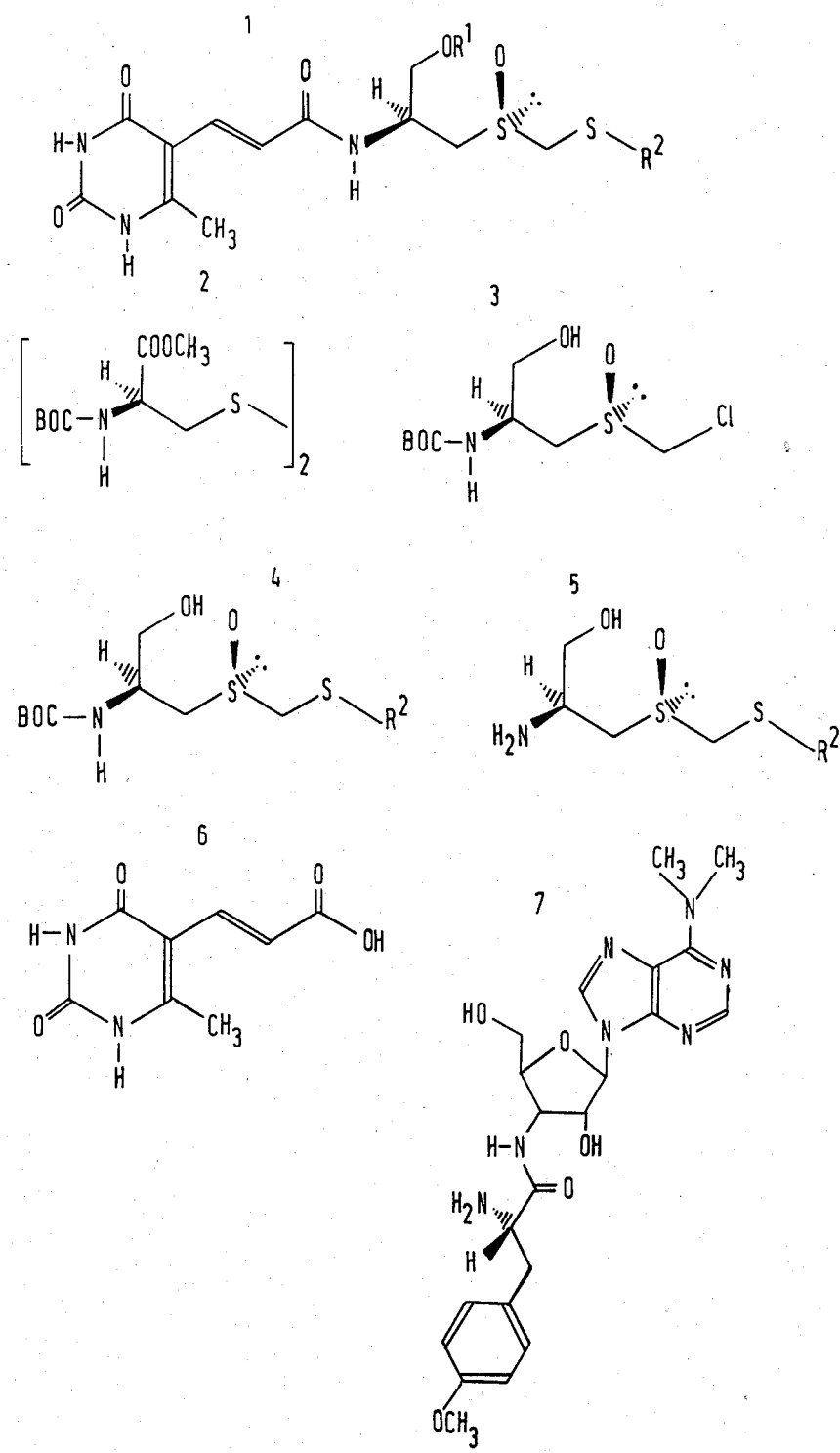

SPARSOMYCIN ($S_c$-$R_s$) DERIVATIVE; PHARMACEUTICAL COMPOSITION HAVING ANTI-TUMOR ACTIVITY

This invention relates to a sparsomycin ($S_c$-$R_s$) derivative having formula 1 of the sheet of formulae, and also relates to a pharmaceutical composition having anti-tumor activity.

Sparsomycin is a metabolite of *Streptomyces sparsogenes* (Antimicrob. Agents Chemother. (1962), 780) and of *Streptomyces cuspidosporus* (Chem. Abstr. (1967), 66, 54328) and has the structure of formula 1 of the sheet of formulae, in which $R^1$ represents hydrogen and $R^2$ represents methyl.

Sparsomycin has attracted much attention on account of its interesting biological activity. This activity is primarily a result of a strong inhibition of the protein biosynthesis resulting in a decline of the protein synthesis and concomitant biological effects. It has been shown (Ann.Rev.Microb. (1971), 25, 488; FEBS Lett. (1974), 40, S63; Molec. Biol. Biochem. Biophys. (1979), 30) that the site of interaction of sparsomycin is in the large ribosomal subunit, where it prevents peptide transfer by interfering with the peptidyl transferase centre. The action of sparsomycin has been demonstrated in prokaryotic cells (L. Slechta: "Antibiotics I", Editors: D. Gottlieb and P. S. Shaw, Springer Verlag, N.Y. (1967), 410; Can. J. Microb. (1967), 62, 595), eukaryotic cells (Biochem.Biophys.Res.Comm. (1966), 23, 453; J.Antibiot. (1978), 31, 598; Biochem. (1977), 16, 3209), including transformed cells (J.Med.Chem. (1977), 20, 337; Antimicrob.Ag.Chemother. (1962), 772; Biochem.Biophys.Acta (1979), 563, 479; Cancer.Res. (1972), 32, 398) and virus-infected cells (J. Virol. (1979), 29, 114; J. Gen.Virol. (1968), 2, 143), and in various cell-free systems (Biochem.Biophys.Acta (1966), 129, 642; Biochem.Biophys. Acta (1976), 447, 460; Proc.-Natl.Acad. Sci. U.S.A. (1968), 61, 726; FEBS Lett. (1975), 52, 236). On the other hand, sparsomycin is not active against whole reticulocytes (Biochem.Biophys. Acta (1966), 119, 109), which is attributed to sparsomycin's being unable to penetrate these cells. The behaviour of sparsomycin with regard to its inhibitory action and its influence on the polyribosomes has also been investigated in vivo (Proc.Natl.Acad.Sci. U.S.A. (1968), 59, 854, J.Natl. Canc.Inst. (1979), 63, 81; Biochem. Pharmacol. (1974), 23, 857).

In connection with the demonstrated activity of sparsomycin against transformed cells and various tumors (Antimicrob.Ag.Chemother. (1962), 772), it has been investigated as a potential cytostatic compound, but clinical tests (Cancer.Chemother.Rep. (1969), 43, 29) revealed eye toxicity.

In order to gain an insight into the biochemical interaction mechanism and the relationship between structure and activity, various researchers have prepared derivatives of Sparsomycin and investigated their activity. In the absence of a total synthesis, however, only a limited number of derivatives could be investigated, which each differed from the sparsomycin itself in various structural parameters. As a result, only limited conclusions could be drawn as to the role of the various structural fragments. Another problem in the interpretation and comparison of the available information as to the relationship between structure and activity in sparsomycin is that the biological activity of the various derivatives has been determined in different systems: in vitro in a KB cell culture (J.Med.Chem. (1977), 20, 337) or in cell-free ribosomal systems (Biochem.Biophys.-Res.Comm. (1977), 75, 563; J.Med.Chem. (1978), 21, 177), in vivo in the P-388 system and the Walker 256 system (J.Pharm,Sci. (1975), 64, 825).

Recently a few total syntheses for sparsomycin and derivatives thereof have become available (J.Am.-Chem.Soc. (1979), 101, 1057; J.Org.Chem. (1981), 46, 3273; J. Org.Chem. (1981), 46, 5408). By means of these total syntheses, an investigation has now been performed, in which various suitable selected derivatives of sparsomycin were prepared and their cytostatic activity investigated in an in-vitro clonogenic L 1210 assay, whereby the inhibition of colony formation was measured.

This investigation surprisingly showed that blocking the hydroxyl group has no significant effect on the activity and that the cytostatic activity can be substantially increased by increasing the lipophilic character of the effector molecule.

The present invention accordingly provides a sparsomycin ($S_c$-$R_s$) derivative having formula 1 of the sheet of formulae, which is characterized in that $R^1$ represents hydrogen, acyl or alkyl, and $R^2$ represents an alkyl group having 2–20 carbon atoms, an aryl group, an aralkyl group or an alkanyl group.

Preferably, according to the invention, $R^1$ represents hydrogen and $R^2$ represents n-octyl or benzyl.

The n-octylsparsomycin is poorly dissolved in water (about 0.2 mg/ml water), whereas benzylsparsomycin is dissolved well in water (1.5 mg/ml water). As a consequence, the use of the latter compound is highly attractive.

The invention also provides a pharmaceutical composition having anti-tumor activity, characterized in that it contains a sparsomycin ($S_c$-$R_s$) derivative according to the invention.

The sparsomycin derivatives according to the invention can be prepared by one of the above total syntheses, in which connection reference is made to the cited literature.

A highly suitable route of preparation starts from BOC-D-cystine methyl ester ($S_c$) having formula 2, in which BOC is the known tert. butyloxycarbonyl group. As described in J.Org.Chem. (1981), 46, 3273, this compound can be converted into the α-chlorosulfoxide having formula 3. This can subsequently be converted by means of a sodium alkyl thiolate $NaSR^2$, e.g. sodium octyl thiolate, $NaS(CH_2)_7CH_3$, or sodium benzyl thiolate, $NaS(CH_2)C_6H_5$, into the cysteinol mono-oxodithioacetal having formula 4, from which, after the removal of the amino-protective group by means of trifluoroacetic acid (TFA) and subsequent deprotonation by means of an ion exchange resin, the amino alcohol having formula 5 can be recovered. Coupling this amino alcohol with β-(6-methyluracilyl)acrylic acid having formula 6 finally gives the desired compound having formula 1, in which $R^1$ is hydrogen. Thereafter, if desired, the hydroxyl group may be acylated or alkylated by means of known per se methods, e.g., a treatment with acetyl chloride and triethylamine to prepare the o-actyl derivative ($R^1$ is $CH_3CO-$).

The higher cytostatic activity of the compounds according to the invention, as compared with sparsomycin itself, is attributed to their lower polar character, owing to the introduction of the lipophilic group $R^2$. Evidently, this leads to a greater affinity to the peptidyl transferase, for the higher activity is observed in both a cell-free system and in-vitro experiments.

It is surprising that blocking the hydroxyl group has no significant results for the activity of the compounds. In fact, analogs of puromycin, which have a hydroxyl group instead of an amino group, are known to undergo a nucleophilic reaction with the peptidyl transfer RNA to form peptidyl-oxypuromycin adducts (Biochem. (1970), 9, 2477). Like sparsomycin, puromycin having formula 7 is an inhibitor of the protein biosynthesis and acts at the same site of the ribosome. Both compounds contain a nucleotide base group, owing to which they can exhibit interaction with ribosomal and/or messenger RNA. Furthermore, both contain a modified amino acid section which, as has been proposed for puromycin, is ultimately responsible for inhibition of progress of the protein synthesis. The molecular mechanism whereby puromycin is capable of inhibiting the protein synthesis comprises an SN(2) type of nucleophilic attack of the puromycin amino group on the carbonyl section of the peptidyl-transfer RNA to form peptidyl-puromycin adducts. On the ground of this data one would have expected sparsomycin to undergo a similar type of interaction as the hydroxy-puromycin analogs, but the blocking of the hydroxyl group has surprisingly been found to have no significant effect on the activity.

The biological activity of the present compounds has been investigated by in-vitro clonogenic assay. Colony assays are much used to measure the response of known lines of animal and human tumor cells to treatment with cytotoxic agents. Recently, for example, the Raji cell culture line of Burkitt's lymphoma (J.Natl. Cancer Inst. (1982), 68, 115) has been used to determine the effect of various anti-cancer medicaments on the capacity of these cells to form colonies in soft agar. The results raise the assumption that known human tumor cell lines can be used for selecting novel anti-cancer medicaments. The growth of tumor colonies in soft agar from primary human tumor explants is still more promising (Nature (1976), 263, 771; and Science (1977), 197, 461).

Results so far show an accuracy of the analysis of 90-95% in predicting clinical resistance and of 60-65% in predicting a clinical response (N.Engl.J.Med. (1978), 298, 1321; and Lancet. (1980), 2, 340). This analysis is possibly of importance as a selection test for novel anti-tumor medicaments (Europ.J.Cancer (1981), 17, 129).

The in-vitro clonogenic assay was effected in leukemia L 1210 cells in soft agar medium (0.3%). There is a good correlation between the activity in vitro and that in vivo of the medicaments investigated. On the basis of the findings in the in-vitro analysis, therefore, the in-vivo activity can be predicted with good results. In the analysis, the inhibition of the L 1210 colony formation by sparsomycin and derivates thereof is determined for various concentrations, and the dose giving 50% inhibition of the colony formation, as compared with non-treated control cells is calculated ($ID_{50}$). The analysis is carried out as follows (variant of the method described in Cancer Chemother.Rep. (1967), 51, 451).

From a suspension culture one hundred L 1210 cells are plated out in 35 mm culture dishes (Falcon) containing 1 ml soft agar culture medium and the compound to be investigated in suitable concentrations. The soft agar culture medium consists of Dulbecco's medium supplemented with 20% horse serum, 60 μmole 2-mercaptoethanol, 20 mg/ml L-asparagine, 75 mg/ml DEAE dextran (molecular weight $2 \times 10^6$) and 0.3% bacto agar (Difco). The culture dishes were incubated at 37° C. in an atmosphere of 10% $CO_2$ in humidified air for 3 days. After this period of continuous exposure to the medicament the colonies were counted and dose-effect curves made. From these curves, the medicament dose is calculated which causes 50% inhibition of the colony formation as compared with non-treated control cells.

The results are summarized in the following Table. These show that blocking the hydroxyl group has no effect on the activity and that the compound n-octylsparsomycin according to the invention has an activity approximately $3 \times$ higher than sparsomycin proper. If the concentrations used are expressed in μmole/ml, n-octylsparsomycin has an activity approximately four times higher.

TABLE 1

| compound, having formula 1, in which | $ID_{50}$ (ng/ml) |
|---|---|
| $R^1 = H$, $R^2 = CH_3$ (sparsomycin) | 150 |
| $R^1 = CH_3CO-$, $R^2 = CH_3$ (O—acetylsparsomycin) | 150 |
| $R^1 = H$, $R^2 = $ n-octyl (invention) | 47 |
| $R^1 = H$, $R^2 = $ benzyl (invention) | 48 |

The activity of the novel compounds was also measured in two cell-free systems, namely Saccharomyces cerevisiae and E. coli, a prokaryotic and a eukaryotic system, respectively. The inhibition of the protein biosynthesis was measured, and this in two ways, by means of both the fragment reaction (R. E. Monro, Methods Enzymol. 1971, 20, 472) and the inhibition of the polyphenylalanine synthesis (N. W. Nirenberg, H. Matthei, Proc.Natl. Acad. Sci. USA 1961, 47, 1588). The results are summarized in the following table. The concentration of sparsomycin or an analog giving 50% inhibition of the protein synthesis relative to the control is given as $ED_{50}$.

TABLE 2

| | $ED_{50}$ (M × $10^6$) | | | |
|---|---|---|---|---|
| | s.c. | | E. coli | |
| compound | fragment reaction | polyphe | fragment reaction | polyphe |
| sparsomycin | 15 | 4.0 | 6.0 | 9.0 |
| O—acetylsparsomycin | 50 | 3.0 | 15.0 | 8.0 |
| n-octylsparsomycin | 180 | 0.35 | 80.0 | 1.5 |
| benzylsparsomyin | * | * | * | 0.8 |

*as yet undetermined

This table shows that octylsparsomycin has a relatively low activity in both a prokaryotic and a eukaryotic system, if tested in the fragment reaction. This reaction is carried out in 30% ethanol in water. It would appear that ethanol reduces the affinity of octylsparsomycin to the ribosomal binding site. This is indicative of a lipophilic character of the interaction between the effector molecule and the binding site. For that matter, this is the first compound to show such a large difference in activity in the two test systems.

Toxicity

The acute $LD_x$ values (lethal dose for x% of the animals) are shown below.

TABLE 3

| compound | $LD_{50}$ (mg per kg mouse; i.p.) | $LD_{10}$ (mg per kg mouse; i.p.) |
|---|---|---|
| sparsomycin | 14.0 | 8.0 |
| n-octylsparsomycin | >30 (i.v.) | * |

TABLE 3-continued

| compound | LD$_{50}$ (mg per kg mouse; i.p.) | LD$_{10}$ (mg per kg mouse; i.p.) |
|---|---|---|
| benzylsparsomycin | * | * |

*as yet undetermined

Pharmacokinetics

Sparsomycin and n-octylsparsomycin in dog, one animal per experiment.

TABLE 4

| | doses mg/kg | AUC* mg. h/l | t½ | Recovery** (% of dose) |
|---|---|---|---|---|
| sparsomycin: i.v. bolus | 0.7 | 1.3 | 1.1 | 24 |
| sparsomycin: i.v. bolus | 1.48 | 10.8 | 2.3 | 55 + 2*** |
| n-octylsparsomycin: i.v. bolus | 0.7 | 1.1 | 1.1 | 0 + 3.4*** |
| n-octylsparsomycin: 4 hrs. infusion | 0.9 | 1.2 | 1.6 | 0 3 |

*AUC area under curve
**in urine
***in gall liquid

In the dogs, no bone marrow depression was observed, but rather a leucocotysis. A reversible, minor hepatic toxicity was observed.

The preparation of the compounds investigated is illustrated in and by the following examples.

EXAMPLE I (comparison)

Sparsomycin (S$_c$-R$_s$)

Sparsomycin (S$_c$-R$_s$) was prepared following the procedure described in J.Org.Chem. (1981), 46, 3273, except that the reactions were carried out while excluding light, and the purification of the end product was modified as follows: chromatography of the crude product over silicagel according to HPLC (eluent CH$_3$OH/CH$_2$Cl$_2$/NH$_4$OH, 80/20/0.2 v/v), followed by gel filtration over Sephadex LH 20 (eluent H$_2$O/CH$_3$OH, 15/85 v/v).

EXAMPLE II (comparison)

O-acetyl-sparsomycin (S$_c$-R$_s$).

To a solution of sparsomycin (46.8 mg, 0.13 mmol) in 5 ml dry pyridine, 3 ml (0.39 mmol) of a 0.13M solution of acetyl chloride in dichloromethane was added. The reaction was stirred overnight at room temperature. After the completion of the reaction, which was monitored by thin layer chromatography (eluent CH$_3$OH/CHCl$_3$, ¼, v/v), 2 ml dry ethanol was added. Thereafter the solvent was evaporated at a reduced pressure, and the crude product was chromatographed over silicagel 60H (HPLC, CH$_3$OH/CH$_2$Cl$_2$, 12/88, v/v). The product was obtained after a final purification over Sephadex LH 20 (eluent H$_2$O/CH$_3$OH, 15/85, v/v) in a yield of 30%. No attempts were made to improve the yield. R$_f$ 0.64 (eluent CH$_3$OH/CHCl$_3$, ¼, v/v); NMR (D$_2$O) δ2.13 (s, 3H, C(O)CH$_3$), 2,31 (s, 3H, SCH$_3$), 2.43 (s, 3H, C(6)CH$_3$), 3.07-3.46 (AB part of the ABX spectrum, 2H, CHCH$_2$S(O), 3.96 and 4.18 (AB spectrum, J$_{AB}$=14 Hz, 2H, S(O)CH$_2$S), 4.20-4.44 (m, 2H, CHCH$_2$O), 4.44-4.70 (m, 1H, CHCH$_2$O), 7.04 and 7.49 (AB spectrum J$_{AB}$=15.5 Hz, 2H, HC=CH).

EXAMPLE III (invention)

n-octyl-sparsomycin (S$_c$-R$_s$)

A solution of sodium octylthiolate (353 mg, 2.1 mmols) in 10 ml dry ethanol was added at once to a stirred solution of the chlorosulfoxide having formula 3 (542 mg, 2 mmols) in 10 ml dry ethanol. The chlorosulfoxide having formula 3 was prepared, and the sodium octylthiolate was checked for purity following the procedures described in J.Org.Chem. (1981), 46, 3273.

Argon was passed through the two solutions for 15 minutes. The reaction mixture was stirred overnight at room temperature. After the completion of the reaction, which was monitored by thin layer chromatography (eluent CH$_3$OH/CH$_2$Cl$_2$.1/9 v/v), the solvent was evaporated and 5 ml water and 3 ml dichloromethane were added. Removal of the turbidity, which was due to finely-divided sodium chloride, could be achieved by stirring with Na$_s$SO$_4$ for about 1 hour. Filtration and removal of the solvent gave the N-protected S-oxo-S[(octylthio)methyl]-D-cysteinol in 85% yield. R$_f$0.45 (eluent CH$_3$OH/CH$_2$Cl$_2$, 1/9, v/v); NMR (CDCl$_3$) δ0.47-2.16 (m, 15H, (CH$_2$)$_6$CH$_3$), 1.44 (s, 9H, t-Bu), 2.56-2.82(m, 2H, SCH(CH$_2$)$_6$CH$_3$), 2.96 and 3.22 (AB part of the ABX spectrum, 8 lines, J$_{AX}$=J$_{BX}$=6 Hz, J$_{AB}$=14 Hz, 2H, CHCH$_2$S(O)), 3.71-3.97 (m, 4H, CH$_2$OH, S(O)CH$_2$S), 3.97-4.28 (br, 1H, CHCH$_2$OH), 5.22-5.33 (br, 1H, NH); Anal. calculated for C$_{17}$H$_{35}$NS$_2$O$_4$: C: 52.53; H: 9.29; N: 3.67. Found: C: 53,68; H: 9.31; N: 3.70.

For the removal of the BOC group, the above compound (190 mg, 0.5 mmol) was dissolved in 10 ml trifluoroacetic acid. The solution was stirred at 0° C. for 30 minutes, whereafter the trifluoroacetic acid was evaporated at a reduced pressure at room temperature. The residue was dried at a reduced pressure over KOH for 1 hour, and then dissolved in a minimum quantity of water. The solution was transferred to an ion exchange column (Amberlite IRA-410, 20-50 mesh OH$^-$ form).

Elution with water and removal of the solvent by freeze drying gave S-oxo-S-[(octylthio)methyl]-D-cysteinol having formula 5, in which R$^2$ represents n-octyl, in a 90% yield. R$_f$0.40 (eluent CH$_3$OH/CHCL$_3$, ¼ v/v); NMR (CD$_2$Cl$_2$) δ0.70-2.20 (m, 15H, (CH$_2$)$_6$CH$_3$) 2.60-2.85 (m, 2H, SCH$_2$, (CH$_2$)$_6$CH$_3$), 2.95 and 3.23 (AN part of the ABC Spectrum, 8 lines, J$_{AX}$=J$_{BX}$=6 Hz, J$_{AB}$=14 Hz, 2H, CHCH$_2$S(O)), 3.70-3.98 (m, 4H, CH$_2$OH, S(O)CH$_2$S), 3.98-4.35 (br, 1H, CHCH$_2$OH).

The n-octyl sparsomycin (S$_c$-R$_s$) was prepared by means of a mixed-anhydride procedure as follows. To a stirred solution, cooled at 0° C., of the acid having formula 6 (112 mg, 0.66 mmol) and triethylamine (86 mg, 0.86 mmol) in 5 ml THF/DMF (1/1, v/v), ethylchloroformate (103 mg, 0.86 mmol) was added. Stirring was continued at 0° C. for 4 hours. Thereafter a solution of the amino alcohol having formula 5, in which R$^2$ represents n-octyl, (140 mg, 0.5 mmol) in 5 ml THF/DMF (1/1, v/v) was added dropwise. The reaction mixture was stirred at room temperature for 48 hours, excluding light.

The solvents were removed at a reduced pressure at room temperature. The crude product was chromatographed over silicagel 60H by HPLC (eluent $CH_3OH/CH_2Cl_2$, $\frac{1}{4}$, v/v), followed by gel filtration over Sephadex LH-20 (eluent $H_2O/CH_3OH$, 15/85, v/v). The product was n-octyl sparsomycin in a yield of 17%; no attempts were made to improve this yield. $R_f$ 0.43 (eluent $CH_3OH/CHCl_2$, $\frac{1}{4}$, v/v); $R_f$ 0.60 or 0.25 (eluents $CH_3OH/H_2O$, 85/15, v/v and 75/25, v/v, HPTLC Merck RP8-F254 plates); $[\alpha]_D^{25} + 77.9$ (c 0.086, $CH_3OH/H_2O$, 1/1, v/v); NMR ($CD_3OD$) $\delta 0.94-1.76$ (m, 15H, $(CH_2)_6CH_3$), 2.35 (s, 3H, $C(6)CH_3$), 2.55-2.84 (m, 2H, $SCH_2(CH_2)_6CH_3$), 2.84-3.49 (m, 2H, $CHCH_2S(O)$), 3.60-3.85 (m, 2H, $CHCH_2OH$), 3.90-4.16 (br.s, 2H, $S(O)CH_2S$), 4.40-4.67 (m, 1H, $CHCH_2OH$), 6.95 and 7.61 (AB spectrum, 2H, $J_{AB} = 15.5$ Hz, HC=CH).

EXAMPLE IV (invention)

Benzylsparsomycin ($S_c$-$R_s$)

A solution of sodium benzylthiolate (350 mg, 2.4 mmols) in 7 ml dry ethanol was added at once to a stirred solution of the chlorosulfoxide having formula 3 (542 mg, 2 mmols, in 10 ml dry ethanol.

The chlorosulfoxide having formula 3 was prepared, and the sodium benzylthiolate checked for purity as described in J. Org.Chem. 1981, 46, 3273. Argon was passed through the two solutions for 15 minutes. After the completion of the reaction, which was monitored by thin-layer chromatography (eluent $CH_3OH/CHCl_3$, 7/93, v/v) the reaction mixture was filtered over celite and rinsed with $CH_2Cl_2$. Subsequently the filtrate was evaporated to dryness and 5 ml water and 30 ml dichloromethane were added. Removal of the turbidity in the organic layer, which was due to finely-divided sodium chloride, could be realised by stirring with $Na_2SO_4$ for about 1 hour. Filtration and removal of the solvents gave the N-protected S-oxo-S[(benzylthio)methyl]-D-cysteinol in a 87% yield. $R_f$ 0.29 (eluent $CH_3OH/CHCl_3$, 7/93, v/v); NMR ($CDCl_3$) $\delta 1.44$ (s, 9H, t-Bu); 2.97 and 3.22 (AB part of ABX-spectrum; 8 lines, $J_{AX} = 6.6$ Hz; $J_{BX} = 6.0$ Hz; $J_{AB} = 13.2$ Hz, $CHCH_2S(O)$); 3.60 and 3.64 (2 lines, 2H, $S(O)CH_2S$); 3.73 (m,2H; $CH_2$—OH); 3.88(s, 2H, S—$CH_2$-$\phi$); 4.06 (m, 2H, CH—$CH_2$—OH); 5,51 (d, 1H, NH, J=9 Hz); 7.28 (br.s, 5H, $C_6H_5$); Anal. calculated for $C_{16}H_{25}NS_2O_4$: C:53.46; H: 7.01; N: 3.90. Found: C: 53.46; H: 6.99; N: 3.92.

For the removal of the Boc group, the above compound (256 mg, 0.713 mmol) was dissolved in 15 ml trifluoroacetic acid. The solution was stirred at 0° C. for 30 minutes, whereafter the trifluoroacetic acid was evaporated in vacuo at room temperature. The residue was dried in vacuo (0.02 mmHg) overnight over KOH. The resulting trifluoroacetic acid salt was, without further characterization, used for the preparation of benzylsparsomycin.

The benzylsparsomycin ($S_c$-$R_s$) was prepared by means of a mixed-anhydride procedure as follows. To a stirred solution of the acid having formula 6 (181 mg, 0.92 mmol) and triethylamine (9.3 mg, 0.92 mmol) in 7 ml THF/DMF (1/1, v/v), cooled at 0° C., isobutylchloroformiate (124 mg, 0.92 mmol) was added. Stirring was continued at 0° C. for 1 hour. Subsequently, a solution of the amino alcohol trifluoroacetic acid salt having formula 5, in which $R^2$ represents benzyl (0.71 mmol) and triethylamine (79 mg, 0.78 mmol) in 7 ml THF/DMF (1/1, v/v) was added dropwise. The reaction mixture was stirred at room temperature for 48 hours with exclusion of light.

The solvents were removed in vacuo at room temperature. The crude product was chromatographed over silicagel 60H by HPLC (eluent $CH_3OH/CH_2Cl_2$, 15/85, v/v), followed by filtration over Sephadex LH-20 (eluent $H_2O/CH_3OH$, 15/85, v/v). The product was benzylsparsomycin in a yield of 37%; no attempts were made to improve this yield. $R_f$ 0.53 (eluent $CH_3OH/CHCl_2$, $\frac{1}{4}$, v/v); $[\alpha]_D^{25} + 121°$ (C=0.135, $H_2O$).

Solubility benzylsparsomycin in $H_2O$ (pH=7) 1.5 mg/ml. Anal. calculated for benzylsparsomycin $C_{19}H_{23}N_3O_5S_2.2H_2O$: M=473.537: C: 48.19; H: 5.74. N: 8.87. Found: C: 48.88; H: 5.30; N: 8.81. NMR ($D_2O$). $\delta 2.42$ (s, 3H, $C(6)CH_3$); 2.77-3.22 (m, 2H, $SCH_2$—S(O)); 3.64-3.77 (m, 2H, $CH_2OH$); 3.88 (s, 2H, S—$CH_2$-$\phi$); 3.95 (br.s, 2H, $S(O)CH_2S$); 4.71 (m, 1H, $CHCH_2OH$); 7.03 and 7.47 (AB spectrum, 2H, $J_{AB} = 16$ Hz, CH=CH); 7.33 (br.s, 5H, $C_6H_5$).

EXAMPLE V

Fragment reaction and polyphenylalanine synthesis

Fragment reaction. The reaction described originally by Monro (see reference in the text) was carried out in 150 μl of 33 mM Tris-HCl pH 7.4, 270 mM KCl, 13 mM magnesium acetate containing 1 mg/ml of ribosomes, $2.10^{-3}$M puromycin, 1 pmol of ($^3$H)Leu-ACCAC(U), the required concentration of sparsomycin analog as indicated in the text and 33% ethanol. The reaction was initiated by the addition of the alcohol and allowed to proceed at 0° C. for 30 min. and then stopped by the addition of 100 μl of 0.3M sodium acetate pH 5.5 saturated with $MgSO_4$. The samples were extracted with 1.5 ml of ethyl acetate and 1 ml of the organic phase was checked for radioactivity.

The 3' terminal pentanucleotide ($^3$H)Leu-ACCAC(U) was prepared from ($^3$H)Leu-tRNA by ribonuclease $T_1$ as described (Monro, as above).

Polyphenylalanine synthesis. The reaction mixture was slightly different for E. coli and for yeast.

E. coli. The reaction mixture (50 μl) contained 65 mM Tris-HCl pH 7.6, 15 mM $MgCl_2$, 90 mM KCl, 15 mM β-mercaptoethanol, 1 mM GTP, 10 mM ATP, 0.2 mg/ml of polyuridylic acid, 1.5 mg/ml of tRNA, 10 μM of ribosomes, 2.5 mg/ml of phosphoenolpyruvate, 20 μg/ml of pyruvate kinase, the required concentration of sparsomycin analog, as indicated in the text, and 5 μl of supernatant fraction S-100. ($^3$H)phenylalanine 30 μM (about 60 cpm/pmol) was added to start the reaction. Incubation was at 37° C. for 30 min. The reaction was stopped by addition of 1 ml of 10% TCA and the samples filtered through glass fiber. The filters were washed with 10 ml of cold 10% TCA, dried and counted for radioactivity.

Yeast. The test was carried out as indicated above for E. Coli but replacing the phosphoenol pyruvate and pyruvate kinase by creatine phosphokinase (50 μg/ml) and creatine phosphate (20 mM). The incubation was performed at 30° C. for 30 min. and the samples processed as above.

In these conditions the control samples polymerized 3 to 8 to 14 molecules of phenylalanine per ribosome in the case of yeast and *E. coli* respectively.

Ribosomes and supernatant fractions from *E. coli* and *Saccharomyces cerevisiae* were prepared according to standard procedures (Staehelin, T. and Maglott D. R. (1971). Methods Enzymol. 20, 449–456; Sánchez-Madrid, F., Reyes, R., Conde, P. and Ballesta, J. P. G. (1979) Eur. J. Biochem. 98, 409–416).

We claim:

1. Sparsomycin ($S_c$-$R_s$) derivative having the formula

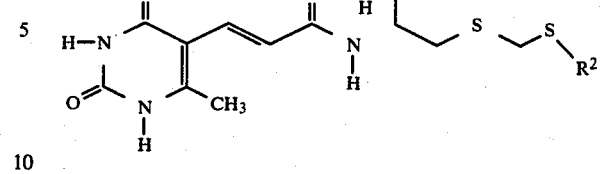

characterized in that $R^1$ represents hydrogen, and with lower alkanoyl or $C_{1-20}$ alkyl, and $R^2$ represents an alkyl group having 2–20 carbon atoms, phenyl, phenyl lower alkyl, or lower alkylphenyl.

2. Sparsomycin ($S_c$-$R_s$) derivative according to claim 1, characterized in that $R^1$ represents hydrogen and $R^2$ represents n-octyl or benzyl.

3. A pharmaceutical composition having an antitumor activity, characterized in that it contains a sparsomycin ($S_c$-$R_s$) derivative according to claim 1 or 2.

* * * * *

UNITED STATES PATENT OFFICE
CERTIFICATE OF CORRECTION

Patent No. 4,581,360        Dated April 8, 1986

Inventor(s) Ottenheijm, et al.

It is certified that error appears in the above-identified patent and that said Letters Patent are hereby corrected as shown below:

[22] Filed: "December 9, 1983" should be

--October 31, 1983--.

Signed and Sealed this

Fifth Day of August 1986

[SEAL]

Attest:

Attesting Officer

DONALD J. QUIGG

Commissioner of Patents and Trademarks